(12) United States Patent
Kuu et al.

(10) Patent No.: US 9,625,210 B2
(45) Date of Patent: *Apr. 18, 2017

(54) OPTIMIZATION OF NUCLEATION AND CRYSTALLIZATION FOR LYOPHILIZATION USING GAP FREEZING

(71) Applicants: BAXTER INTERNATIONAL INC., Deerfield, IL (US); BAXTER HEALTHCARE SA, Glattppark (Opfikon) (CH)

(72) Inventors: Wei-Youh Kuu, Libertyville, IL (US); Mark J. Doty, Grayslake, IL (US); William S. Hurst, Burlington, WI (US); Christine L. Rebbeck, Lake Barrington, IL (US)

(73) Assignees: BAXTER INTERNATIONAL INC., Deerfield, IL (US); BAXTER HEALTHCARE SA, Glattpark (Opfikon) (CH)

(*) Notice: Subject to any disclaimer, the term of this patent is extended or adjusted under 35 U.S.C. 154(b) by 22 days.

This patent is subject to a terminal disclaimer.

(21) Appl. No.: 14/543,627

(22) Filed: Nov. 17, 2014

(65) Prior Publication Data

US 2015/0184935 A1 Jul. 2, 2015

Related U.S. Application Data

(63) Continuation of application No. 13/432,498, filed on Mar. 28, 2012, now Pat. No. 8,966,782, which is a (Continued)

(51) Int. Cl.
*F26B 5/06* (2006.01)
*G01N 21/68* (2006.01)
(Continued)

(52) U.S. Cl.
CPC .............. *F26B 5/06* (2013.01); *F25C 1/00* (2013.01); *F25D 17/02* (2013.01); *G01N 21/68* (2013.01)

(58) Field of Classification Search
CPC ...... F26B 3/00; F26B 5/00; F26B 5/06; F25D 17/00; F25D 17/02; F25C 1/00; G01N 21/68
(Continued)

(56) References Cited

U.S. PATENT DOCUMENTS 3,199,217 A 8/1965 Oldenkamp et al.
3,245,152 A 4/1966 Natelson et al.
(Continued)

FOREIGN PATENT DOCUMENTS

CH EP 2450033 A1 * 5/2012 ............... A61K 9/19
DE 2235483 A1 1/1974
(Continued)

OTHER PUBLICATIONS

Bursac et al., A practical method for resolving the nucleation problem in lyophilization, BioProcess International (Oct. 2009).
(Continued)

*Primary Examiner* — Stephen M Gravini
(74) *Attorney, Agent, or Firm* — Marshall, Gerstein & Borun LLP

(57) ABSTRACT

This application discloses devices, articles, and methods useful for producing lyophilized cakes of solutes. The devices and articles provide for a method of freezing liquid solutions of the solute by the top and the bottom of the solution simultaneously and at approximately the same rate. The as frozen solution can then provide a lyophilized cake of the solutes with large and uniform pores.

20 Claims, 14 Drawing Sheets

Related U.S. Application Data continuation-in-part of application No. 13/246,342, filed on Sep. 27, 2011, now Pat. No. 8,689,460.

(60) Provisional application No. 61/387,295, filed on Sep. 28, 2010.

(51) Int. Cl.
*F25C 1/00* (2006.01)
*F25D 17/02* (2006.01)

(58) Field of Classification Search
USPC .......... 34/284, 287; 62/66; 604/82, 187, 416
See application file for complete search history.

(56) References Cited

U.S. PATENT DOCUMENTS

| | | | |
|---|---|---|---|
| 3,270,434 A | 9/1966 | Hackenberg et al. | |
| 3,289,314 A | 12/1966 | Della Porta | |
| 4,177,577 A | 12/1979 | Bird | |
| 4,501,719 A | 2/1985 | Williams | |
| 4,953,299 A | 9/1990 | Gimeno et al. | |
| 5,035,065 A | 7/1991 | Parkinson | |
| 5,727,333 A | 3/1998 | Folan | |
| 5,884,413 A * | 3/1999 | Anger | F26B 5/06 34/92 |
| 6,199,297 B1 | 3/2001 | Wisniewski | |
| 6,920,701 B2 * | 7/2005 | Haseley | F26B 5/06 34/92 |
| 7,334,346 B2 * | 2/2008 | Nomine | F26B 5/06 34/284 |
| 8,137,444 B2 | 3/2012 | Farsad et al. | |
| 8,371,039 B2 * | 2/2013 | Kuu | A61K 9/19 165/185 |
| 8,544,183 B2 * | 10/2013 | Kuu | A61K 9/19 165/185 |
| 8,689,460 B2 | 4/2014 | Kuu | |
| 8,793,896 B2 | 8/2014 | Patel et al. | |
| 8,966,782 B2 * | 3/2015 | Kuu | F26B 5/06 34/287 |
| 9,121,637 B2 * | 9/2015 | Ling | F26B 5/06 |
| 2001/0056272 A1 | 12/2001 | Yagi et al. | |
| 2003/0015825 A1 | 1/2003 | Sugie et al. | |
| 2005/0086630 A1 | 4/2005 | Zukor et al. | |
| 2007/0186437 A1 | 8/2007 | Gasteyer et al. | |
| 2007/0186567 A1 | 8/2007 | Gasteyer et al. | |
| 2008/0276482 A1 | 11/2008 | Broughall et al. | |
| 2010/0107437 A1 | 5/2010 | Ogata et al. | |
| 2010/0229725 A1 | 9/2010 | Farsad et al. | |
| 2010/0230830 A1 | 9/2010 | Farsad et al. | |
| 2010/0242301 A1 | 9/2010 | Rampersad et al. | |
| 2011/0154681 A1 | 6/2011 | Kuu et al. | |
| 2011/0154682 A1 | 6/2011 | Kuu et al. | |
| 2012/0077971 A1 | 3/2012 | Kuu | |
| 2012/0192448 A1 | 8/2012 | Kuu et al. | |
| 2013/0059005 A1 | 3/2013 | Turchetta et al. | |

FOREIGN PATENT DOCUMENTS

| | | |
|---|---|---|
| DE | 10233703 A1 | 2/2004 |
| EP | 1452099 A1 | 9/2004 |
| FR | 2580473 A1 | 10/1986 |
| FR | 2607129 A1 | 5/1988 |
| FR | 2857961 A1 | 1/2005 |
| GB | 1427676 A | 3/1976 |
| JP | 2-128095 A | 10/1990 |
| JP | 2003169639 | 6/2003 |
| JP | 2007223857 | 9/2007 |
| JP | 61234764 | 10/2008 |
| JP | 2009518640 A | 5/2009 |
| WO | WO-91/07085 A2 | 5/1991 |
| WO | WO-01/57121 A1 | 8/2001 |
| WO | WO-03/047368 | 6/2003 |
| WO | WO-2012/054194 | 4/2012 |

OTHER PUBLICATIONS

Ho et al., Lyophilization of pharmaceutical injections: theoretical physical model, J. Pharm. Sci., 68(9):1170-4 (1979).

Hottot et al., Experimental study and modeling of freeze-drying in syringe configuration. Part I: Freezing step, Drying Technol., 27:40-8 (2009).

Hottot et al., Experimental study and modeling of freeze-drying in syringe configuration. Part II: Mass and heat transfer parameteres and sublimation end-points, Drying Technol., 27:49-58 (2009).

International Search Report and Written Opinion for corresponding International application No. PCT/US2011/053462, mailing date Feb. 10, 2012.

International Search Report and Written Opinion for international application No. PCT/US2012/030854, mailing date Dec. 13, 2012.

Kasper et al., The freezing step in lyophilization: physico-chemical fundamentals, freezing methods and consequences on process performance and quality attributes of biopharmaceuticals, Eur. J. Pharm. Biopharm., 78:248-63 (2011).

Kasraian et al., The effect of tertiary butyl alcohol on the resistance of the dry product layer during primary drying, Pharm. Res., 12(4):491-5 (1995).

Konstantinidis et al., Controlled nucleation in freeze-drying: effects on pore size in the dried product layer, mass transfer resistance, and primary drying rate, J. Pharm. Sci., 100(8):3453-70 (2011).

Kramer et al., Freeze-drying using vacuum-induced surface freezing, J. Pharm. Sci., 91(2):433-43 (2002).

Kuu et al., Determination of shelf heat transfer coefficients along the shelf flow path of a freeze dryer using the shelf fluid temperature perturbation approach, Pharm. Dev. Tec., 12:485-94 (2007).

Kuu et al., Product mass transfer resistance directly determined during freeze-drying cycle runs using tunable diode laser absorption spectroscopy (TDLAS) and pore diffusion model, Pharm. Dev. Tech., pp. 1-11 Early Online (2010).

Kuu et al., Rapid determination of dry layer mass transfer resistance for various pharmaceutical formulations during primary drying using product temperature profiles, Int. J. Pharm., 313:99-113 (2006).

Kuu et al., Rapid determination of vial heat transfer parameters using tunable diode laser absorption spectroscopy (TDLAS) in response to step-changes in pressure set-point during freeze-drying, J. Pharm. Sci., 98(3):1136-54 (2009).

Kuu et al., Rapid freeze-drying cycle optimization using computer programs developed based on heat and mass transfer models and facilitated by tunable diode laser absorption spectroscopy (TDLAS). J. Pharm. Sci., 98(9):3469-82 (2009).

Liu et al., A study of the impact of freezing on the lyophilization of a concentrated formulation with a high fill depth, Pharm. Dev. Tech., 10:261-72 (2005).

Lu et al., Freeze-drying of mannitol-trehalose-sodium chloride-based formulations: the impact of annealing on dry layer resistance to mass transfer and cake structure, Pharm. Dev. Technol., 9(1):85-95 (2004).

Omega Engineering Inc. website, downloaded from the Internet at: <www.omega.com>.

Patel et al., Freeze-drying in novel container system: characterization of heat and mass transfer in glass syringes, J. Pharm. Sci., 99&7):3188-204 (2010).

Pikal et al., Mass and heat transfer in vial freeze-drying of pharmaceuticals: role of the vial, J. Pharm. Sci., 73:1224-37 (1984).

Pikal et al., Physical chemistry of freeze-drying: measurement of sublimation rates for frozen aqueous solutions by a microbalance technique, J. Pharm. Sci., 72(6):635-50 (1983).

Pikal et al., The impact of the freezing stage in lyophilization: effects of the ice nucleation temperature on process design and product quality, Am. Pharm. Rev., 5:48-52 (2002).

Pikal et al., Use of laboratory data in freeze drying process design: Heat and mass transfer coefficients and the computer simulation of freeze drying, J. Parenteral Sci. and Tech., 39(3):11538 (1985).

Rambahtla et al., Heat and mass transfer scale-up issues during freeze drying; II. Control and characterization of the degree of supercooling, AAPS Pharm. Sci. Tech., 5(4):Article 58 (2004).

(56) References Cited

OTHER PUBLICATIONS

Randolph et al., Freezing and annealing phenomena in lyophilization: effects upon primary drying rate, mophology, and heterogeneity, Am. Pharm. Rev., 5:40-7 (2002).

Schwegman et al., Evidence of partial unfolding of proteins at the ice/freeze-concentrate interface by infrared microscopy, J. Pharm. Sci., 98:3239-46 (2009).

Searles et al., Annealing to optimize the primary drying rate, reduce freezing-induced drying rate heterogenity, and determine TgO in pharmaceutical lyophilization, J. Pharm. Sci., 90:872-87 (2001).

Searles et al., Primary drying rate heterogeneity druing pharmaceutical lyophilization, Am. Pharm. Rev., 3:6-24 (2000).

Searles et al., The ice nucleation temperature determines the primary drying rate of lyophilization for samples frozen on a temperature-controlled shelf, J. Pharm. Sci., 90(7):860-71 (2001).

Searles, Freezing and annealing phenomena in lyophilization IN: Rey et al. (eds.), Freeze-Drying Lyophilization of Pharmaceutical and Biological Products, New York: Marcel Dekker, Inc. (2004).

\* cited by examiner

OPTIMIZATION OF NUCLEATION AND CRYSTALLIZATION FOR LYOPHILIZATION USING GAP FREEZING

CROSS-REFERENCE TO RELATED APPLICATION

This is a continuation of U.S. patent application Ser. No. 13/432,498, filed Mar. 28, 2012 which is a continuation-in-part of U.S. patent application Ser. No. 13/246,342, filed, Sep. 27, 2011, and the benefit under 35 U.S.C. §119(e) of U.S. Provisional Patent Application Ser. No. 61/387,295 filed Sep. 28, 2010, is also hereby claimed. The disclosures of the foregoing applications are hereby incorporated herein by reference.

FIELD OF DISCLOSURE

This disclosure relates to methods and apparatus used for lyophilizing liquid solutions of solutes. The disclosure provides a method for optimization of the nucleation and crystallization of the liquid solution during freezing to produce lyophilized cakes of the solutes with large, consistent pore sizes. The disclosure also provides a method for rapid lyophilization of the frozen liquid solution. The disclosure additionally provides apparatus for use with the method and lyophilization chambers.

BRIEF DESCRIPTION OF RELATED TECHNOLOGY

The preservation of materials encompasses a variety of methods. One important method, lyophilization, involves the freeze-drying of solutes. Typically, a solution is loaded into a lyophilization chamber, the solution is frozen, and the frozen solvent is removed by sublimation under reduced pressure.

One well known issue associated with the lyophilization of materials (e.g., sugars) is the formation of one or more layers of the solute (the dissolved materials) on the top of the frozen solution. In a worse case, the solute forms an amorphous solid that is nearly impermeable and eventually prevents sublimation of the frozen solvent. These layers of concentrated solute can inhibit the sublimation of the frozen solvent and may require use of higher drying temperatures and/or longer drying times. The higher drying temperatures may negatively impact the integrity of the solute and the longer drying time may have a negative effect on the economics of the process.

SUMMARY

One embodiment of the invention is an article adapted for use in a lyophilization chamber comprising a heat sink with a heat sink surface in thermal communication with a refrigerant; a tray surface; and a thermal insulator disposed between the heat sink surface and the tray surface. The article can include a refrigerant conduit in thermal communication with the heat sink surface and a heat sink medium disposed between the refrigerant conduit and the heat sink surface.

The thermal insulator can form a fixed distance, for example greater than about 0.5 mm, separating the heat sink surface and tray surface during one or more steps in a lyophilization process. The distance can be maintained by the insulator comprising a spacer disposed between the heat sink surface and the tray surface, the spacer having a thickness of greater than, for example, about 0.5 mm. In an embodiment the thermal insulator can support a tray carrying the tray surface. In a further embodiment the thermal insulator can form the tray surface.

An additional embodiment of the invention is the lyophilization device that includes the article. In this embodiment, the lyophilization device can include a plurality of heat sinks that individually have a heat sink surface in thermal communication with a refrigerant, at least one of said heat sinks being disposed above another to thereby form upper and lower heat sinks; a tray surface disposed between the upper heat sink and a lower heat sink surface; and a thermal insulator is disposed between the tray surface and the lower heat sink.

The lyophilization device can have the distance from the heat sink surface to the tray surface fixed by the thermal insulator. The thermal insulator can comprise the spacer, or a brace affixed to an internal wall (fixed or adjustable) of the lyophilization device or other embodiments can maintain a distance between the lower heat sink surface and the tray surface during one or more steps in the lyophilization process.

Still another embodiment of the invention is a vial comprising a sealable sample container having top and a bottom and a thermal insulator comprises a thermally insulating support affixed to the bottom of the sealable sample container, the thermally insulating support having a thermal conductivity less than about 0.2 W/mK at 25° C. Where the sample container and the insulating support are made of different materials.

Yet another embodiment is a method of lyophilizing a liquid solution using the article, lyophilization device and/or vial described herein. The method includes loading a container comprising a liquid solution into a lyophilization chamber comprising a heat sink; the liquid solution comprising a solute and a solvent and characterized by a top surface and a bottom surface; providing a thermal insulator between the container and the heat sink; lowering the temperature of the heat sink and thereby the ambient temperature in the lyophilization chamber comprising the container to a temperature sufficient to freeze the liquid solution from the top and the bottom surfaces at approximately the same temperature and form a frozen solution. The method then includes lyophilizing the frozen solution by reducing the ambient pressure. In a further embodiment the method may comprise removing the thermal insulator before or during the lyophilizing step.

The method can include the lyophilization chamber having a plurality of heat sinks and loading the container comprising the liquid solution into the lyophilization chamber between two parallel heat sinks.

A further embodiment of the invention includes a method of freezing a liquid solution for subsequent lyophilization, the liquid comprising top and bottom surfaces and disposed in a container, and the container disposed in a lyophilization chamber comprising a heat sink, the improvement comprising forming the a thermal insulator by separating the container from direct contact with the heat sink, to thereby freeze the solution from the top and bottom surfaces at approximately the same temperature.

Still another embodiment of the invention is a lyophilized cake comprising a substantially dry lyophilized material; and a plurality of pores in the lyophilized material having substantially the same pore size; wherein the lyophilized cake was made by the method disclosed herein. The lyophilized cake can have a pore size that is substantially larger than the pore size of a reference lyophilized cake comprising the same material as the lyophilized cake but made by a reference method comprising loading a container comprising a liquid solution into a lyophilization chamber comprising a heat sink; the liquid solution comprising the material and a solvent; excluding a thermal insulator between the container and the heat sink; lowering the temperature of the heat sink and thereby the ambient temperature in the lyophilization chamber to freeze the liquid solution; freezing the liquid solution; and lyophilizing the frozen solution to form the reference lyophilized cake.

Yet another aspect of the invention is a method including providing a lyophilization chamber including a heat sink surface in thermal communication with a refrigerant, loading a container including a liquid solution into the lyophilization chamber, the liquid solution including a solute and a solvent and characterized by a top surface and a bottom surface, and lowering the temperature of the heat sink and thereby the ambient temperature in the lyophilization chamber holding the container to a temperature sufficient to freeze the liquid solution, wherein the container is loaded into the lyophilization chamber at a distance spaced vertically from the heat sink thereby forming an intervening thermal insulator, the distance selected to provide freezing the liquid solution from the top and the bottom surfaces at approximately the same temperature and thereby form a frozen solution.

In any one of the methods described herein employing a thermal insulator between container and heat sink during freezing, it is further contemplated that the thermal insulator may be removed thereby placing the container in thermally-conductive contact (i.e., direct or indirect) with the heat sink during or following freezing of the solution, to thereby facilitate more rapid freeze drying in the sublimation process.

BRIEF DESCRIPTION OF THE DRAWING FIGURES

For a more complete understanding of the disclosure, reference should be made to the following detailed description and accompanying drawing figures wherein.

Figure 6:
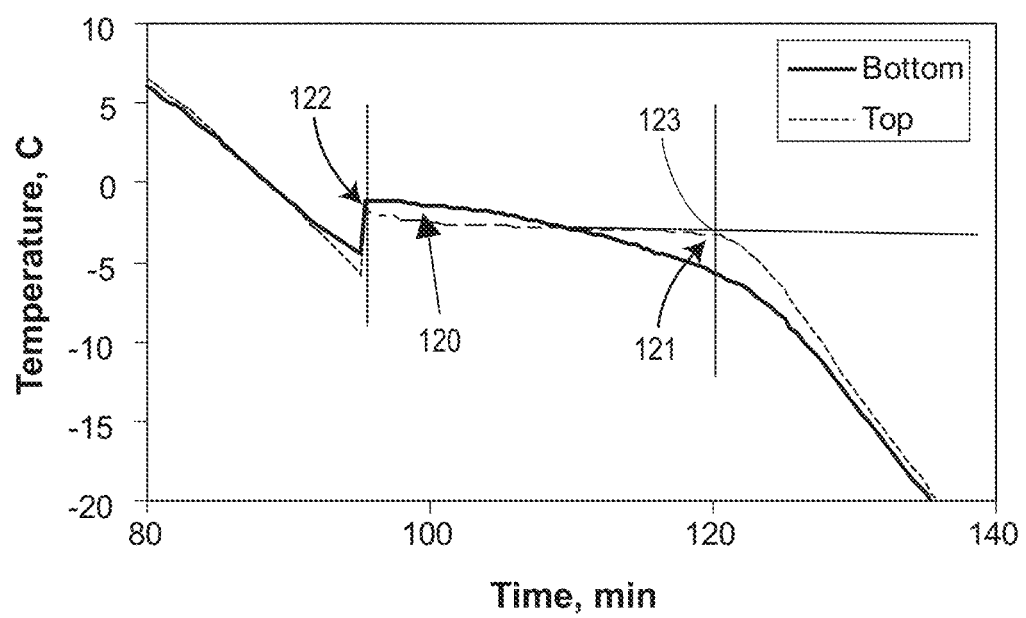
Figure 7A:
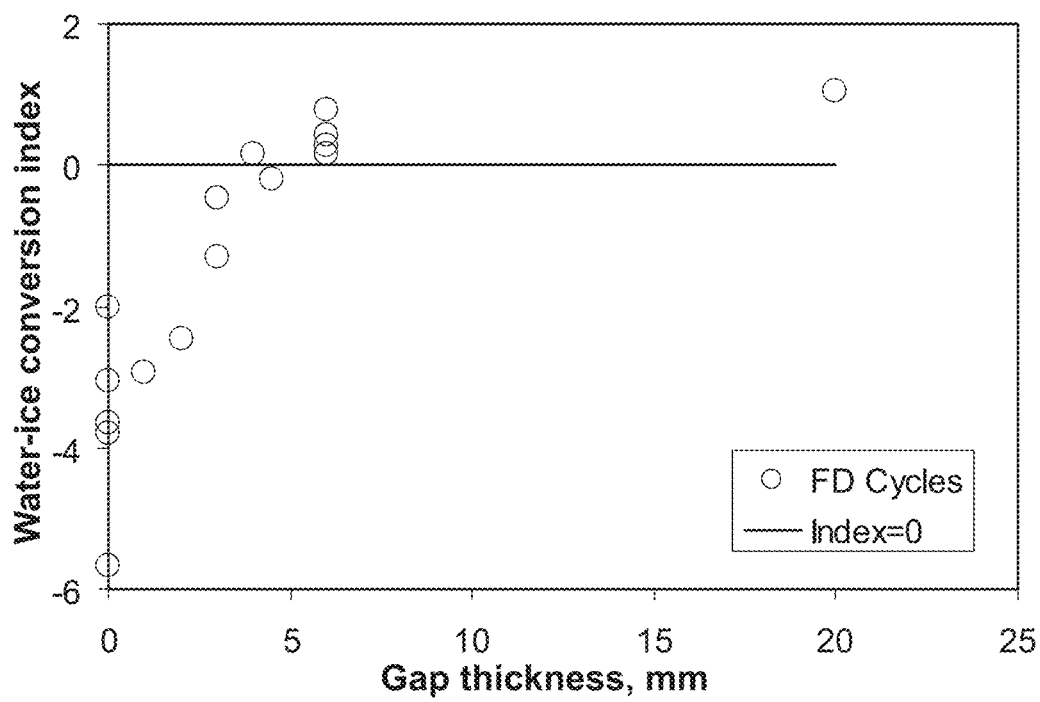
Figure 7B:
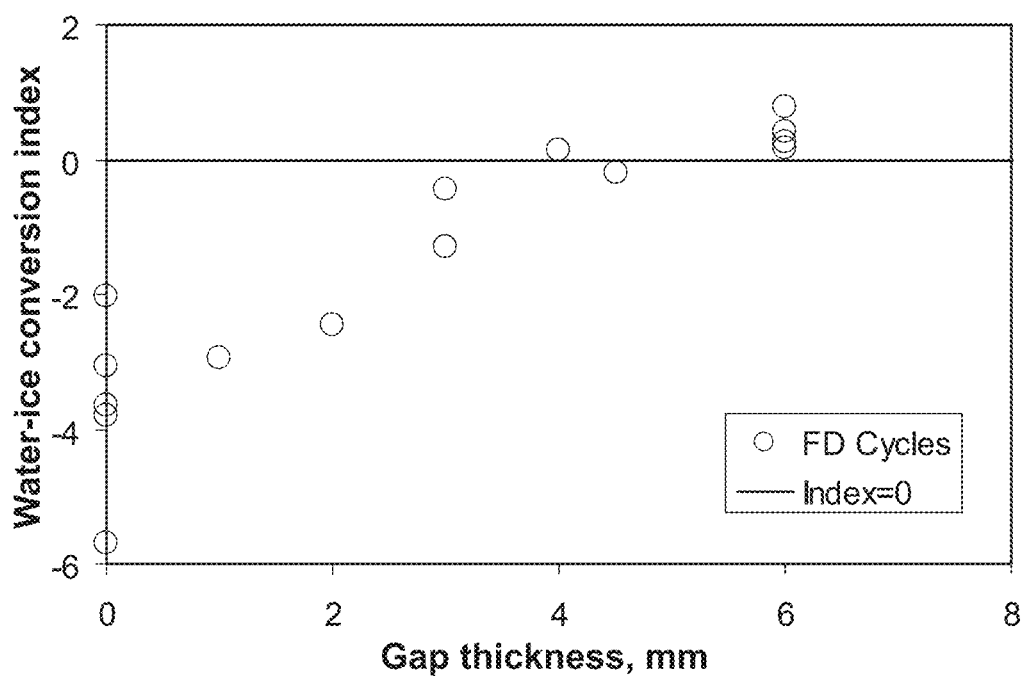
Figure 8:
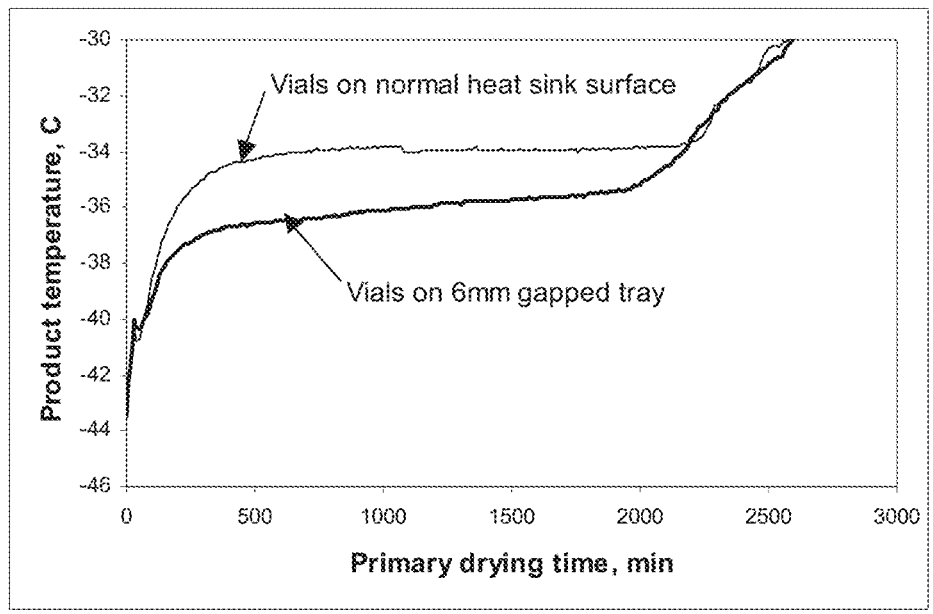
Figure 9:
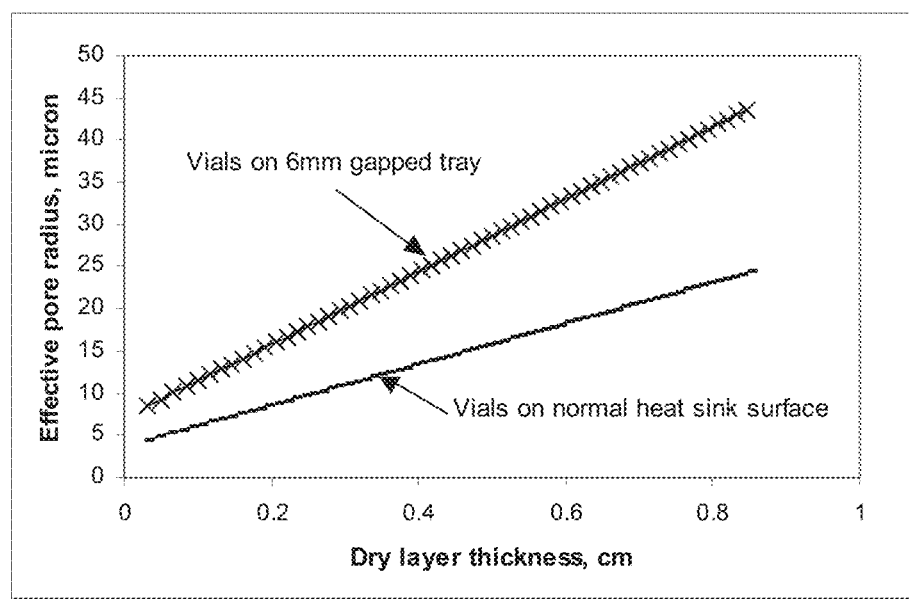
Figure 10:
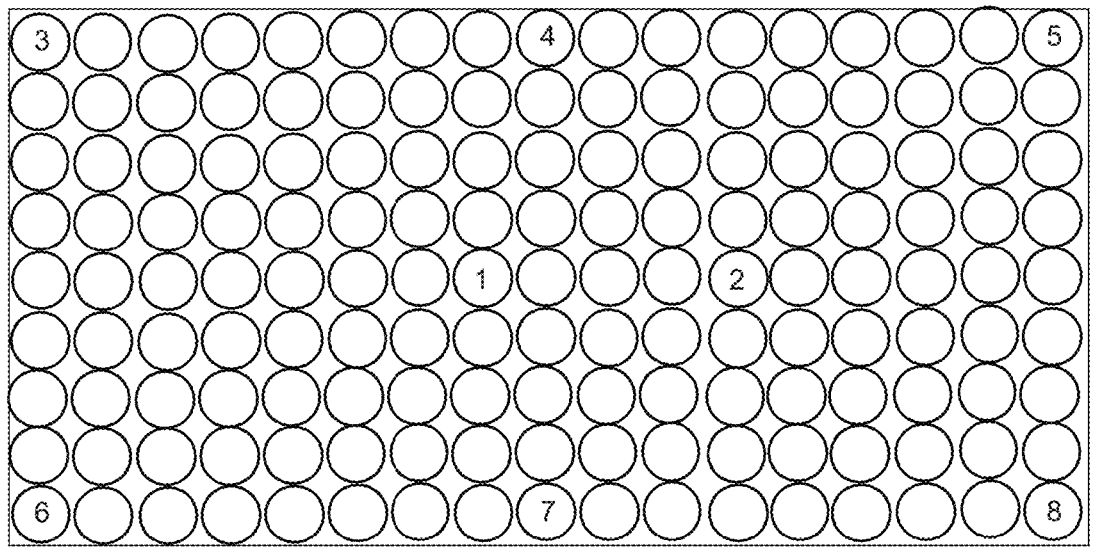
Figure 11:
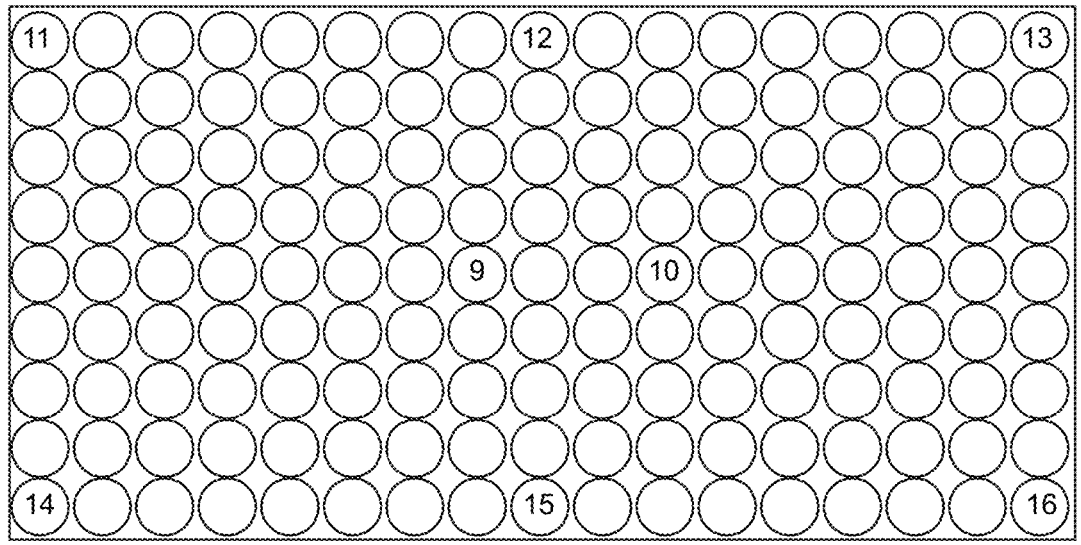
Figure 12:
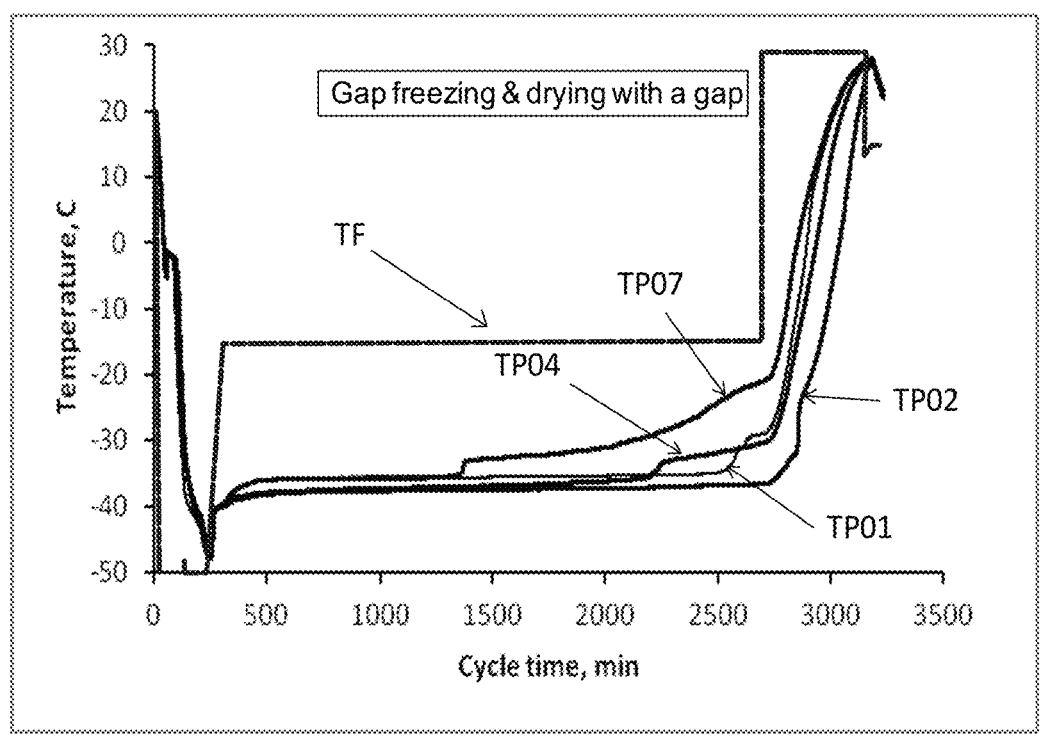
Figure 13:
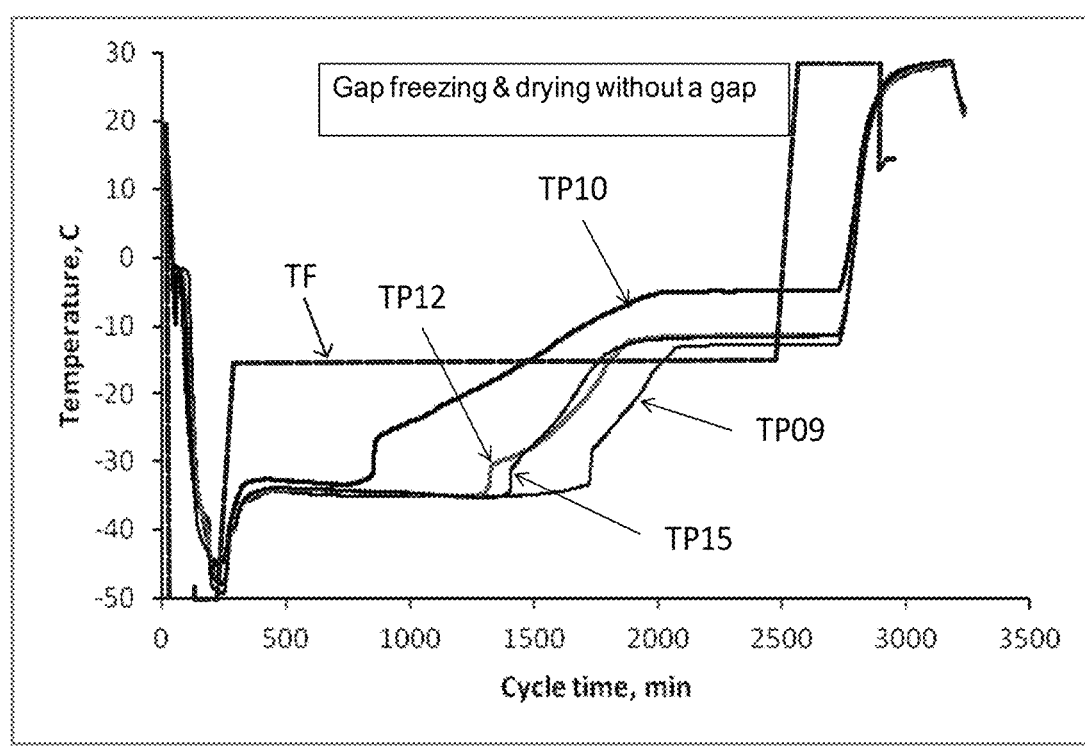
Figure 14:
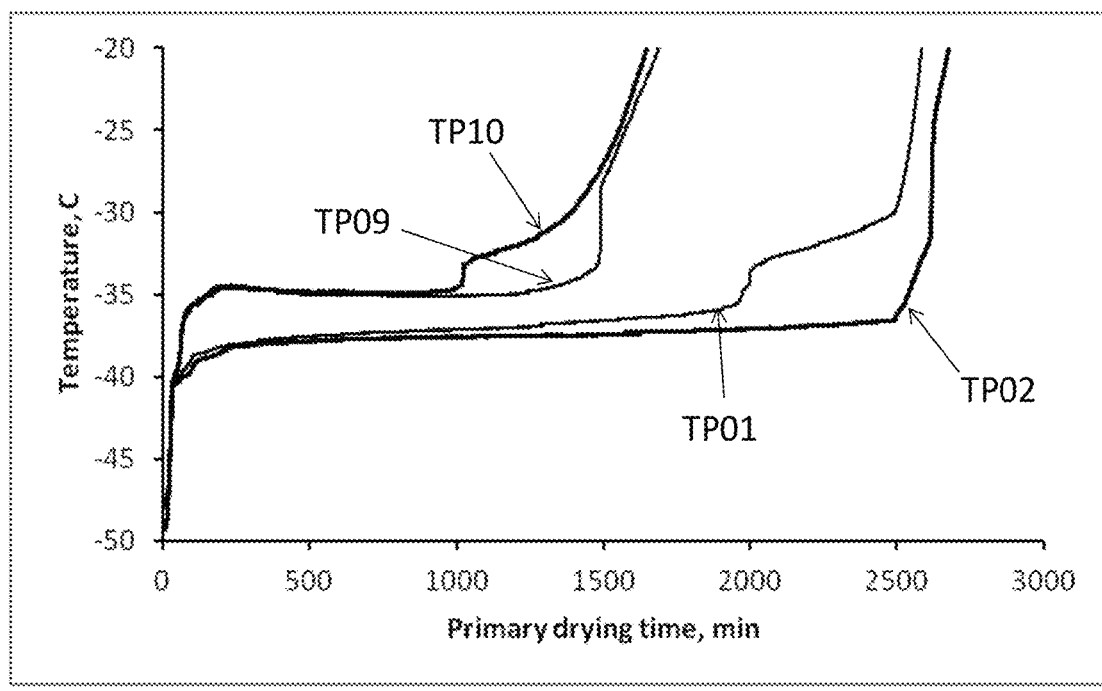
Figure 15:
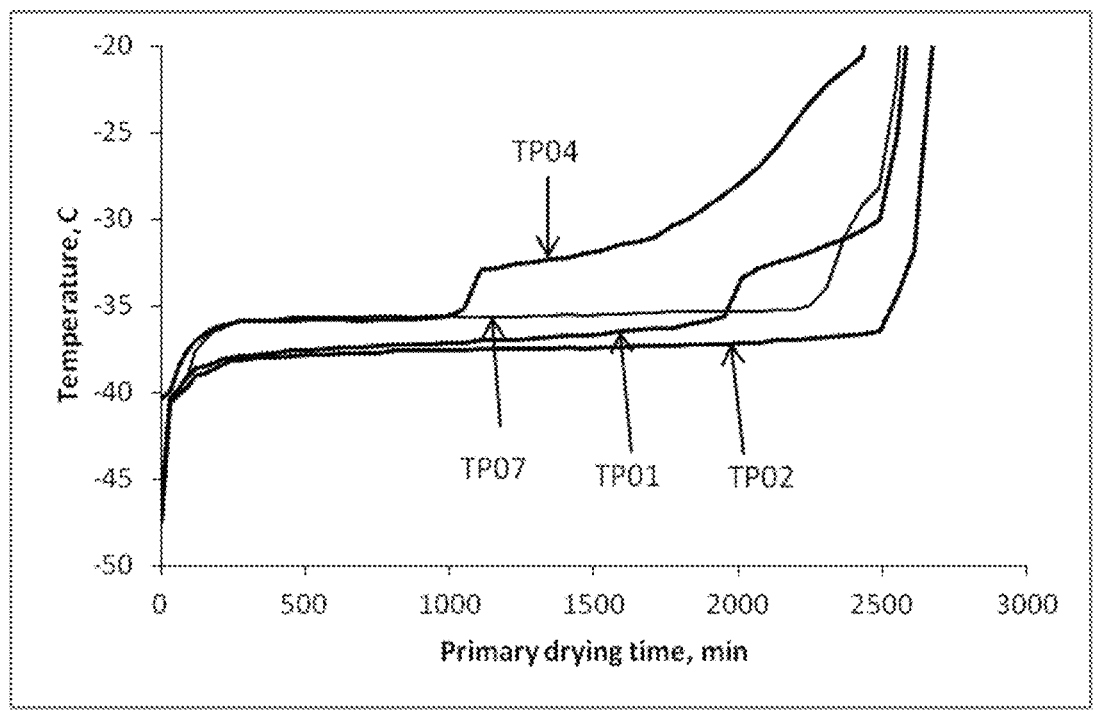
Figure 16:
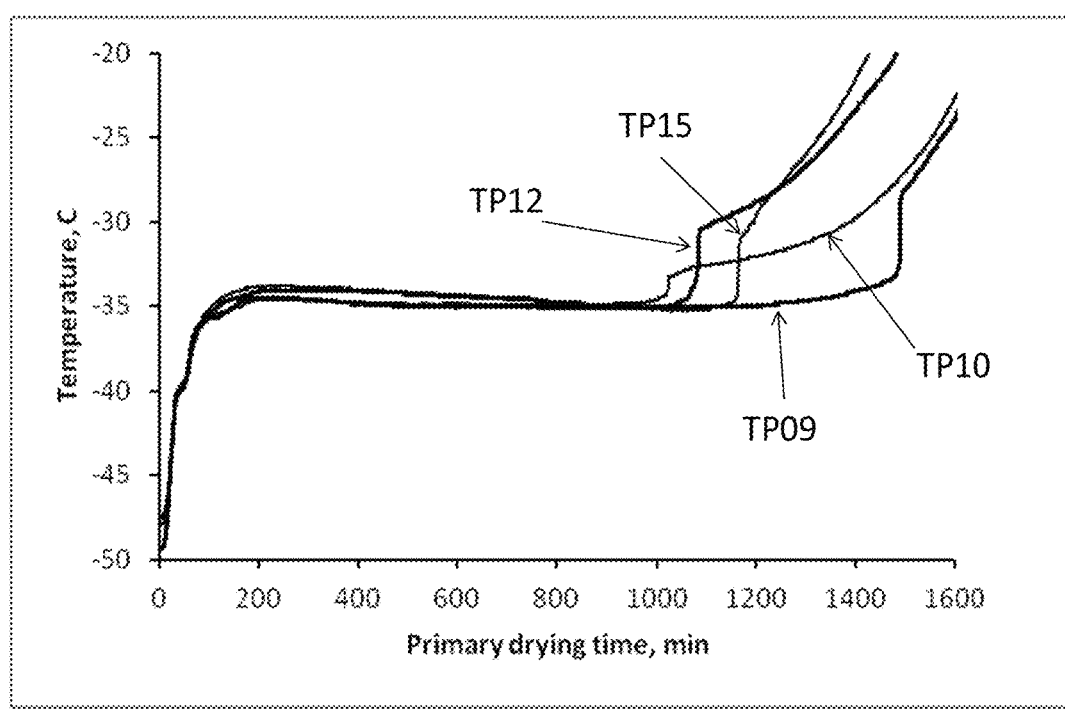

FIG. 6 is a plot of the temperatures of the top and the bottom of a 10 wt. % aqueous sucrose solution frozen using a 3 mm gap between a heat sink surface and a tray (the tray having a thickness of about 1.2 mm) showing a nucleation event, the differences in temperatures between the top and the bottom of the solution, and the reduction in temperature of the top of the solution after the freezing point plateau;

FIGS. 7A and 7B are plots of the water-ice conversion indices for a 5 wt. % aqueous sucrose solution as a function of distance (air gap) from a heat sink surface to a tray (the tray having a thickness of about 1.2 mm), wherein FIG. 7A plots gap thicknesses over the range of 0-25 mm and FIG. 7B plots gap thicknesses over the range 0-8 mm;

FIG. 8 is a plot of the internal temperatures of vials during a primary drying process illustrating the effect of gap-freezing on the product temperature during freeze-drying;

FIG. 9 is a plot of effective pore radii for samples frozen on a 6 mm gapped tray and samples frozen directly on the heat sink surface;

FIGS. 10 and 11 are temperature probe diagrams for top shelf and bottom shelf vials according to Example 2;

FIGS. 12 and 13 are comparisons of approximate drying time for vials on the top shelf and bottom shelf, according to Example 2;

FIG. 14 is a comparison of product temperatures of top shelf center vials and bottom shelf center vials during drying, according to Example 2;

FIG. 15 is a comparison of product temperatures of top shelf center vials and edge vials TP04 and TP07 during drying, according to Example 2; and FIG. 16 is a comparison of product temperatures of bottom shelf center vials and edge vials during drying, according to Example 2.

While the disclosed methods and articles are susceptible of embodiments in various forms, there are illustrated in the examples and figures (and will hereafter be described) specific embodiments of the methods and articles, with the understanding that the disclosure is intended to be illustrative, and is not intended to limit the invention to the specific embodiments described and illustrated herein.

DETAILED DESCRIPTION

One well known issue associated with the lyophilization of materials (e.g., sugars) is the formation of one or more layers of the solute (the dissolved materials) on the top of the frozen solution. These layers form during the freezing of the solution because, typically, the solutions are positioned within the lyophilization chamber on a heat sink which rapidly decreases in temperature and causes the solution to freeze from the bottom up. This bottom up freezing pushes the solute in the liquid phase closer to the top of the solution and increases the solute concentration in the still liquid solution. The high concentration of solute can then form a solid mass that can inhibit the flow of gasses therethrough. In a worse case, the solute forms an amorphous solid that is nearly impermeable and prevents sublimation of the frozen solvent. These layers of concentrated solute can inhibit the sublimation of the frozen solvent and may require use of higher drying temperatures and/or longer drying times.

Disclosed herein is an apparatus for and method of freezing a material, e.g., for subsequent lyophilization, that can prevent the formation of these layers and thereby provide efficient sublimation of the frozen solvent.

The lyophilization or freeze drying of solutes is the sublimation of frozen liquids, leaving a non-subliming material as a resultant product. Herein, the non-subliming material is generally referred to as a solute. A common lyophilization procedure involves loading a lyophilization chamber with a container that contains a liquid solution of at least one solute. The liquid solution is then frozen. After freezing, the pressure in the chamber is reduced sufficiently to sublime the frozen solvent, such as water, from the frozen solution.

The lyophilization device or chamber is adapted for the freeze drying of samples in containers by including at least one tray for supporting the container and means for reducing the pressure in the chamber (e.g., a vacuum pump). Many lyophilization devices and chambers are commercially available.

Figure 1:
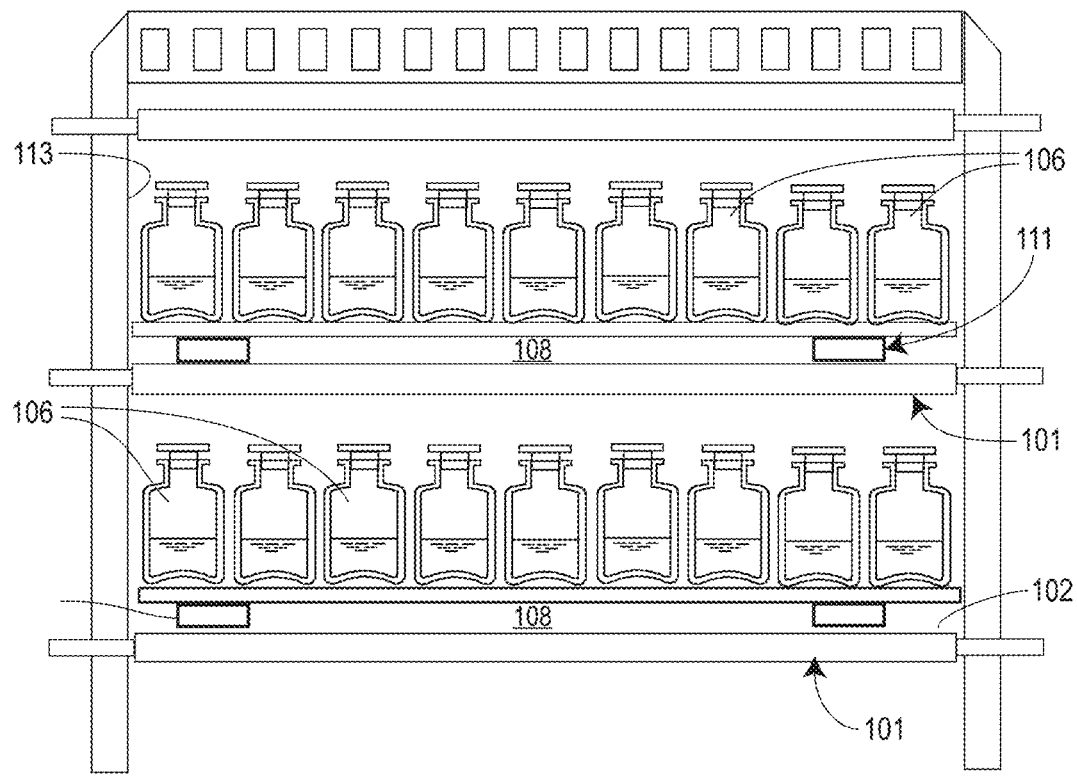
FIG. 1 is a drawing of the inside of a lyophilization device showing a lyophilization chamber and a plurality of heat sinks in a vertical arrangement.
Figure 2:
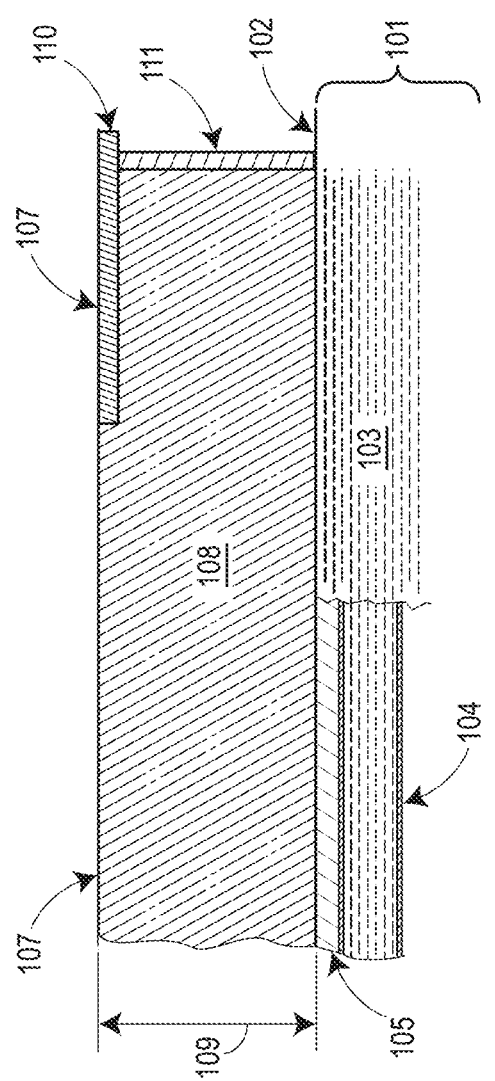
FIG. 2 is a composite drawing of an article showing an arrangement of a heat sink surface and a tray surface.
Figure 3:
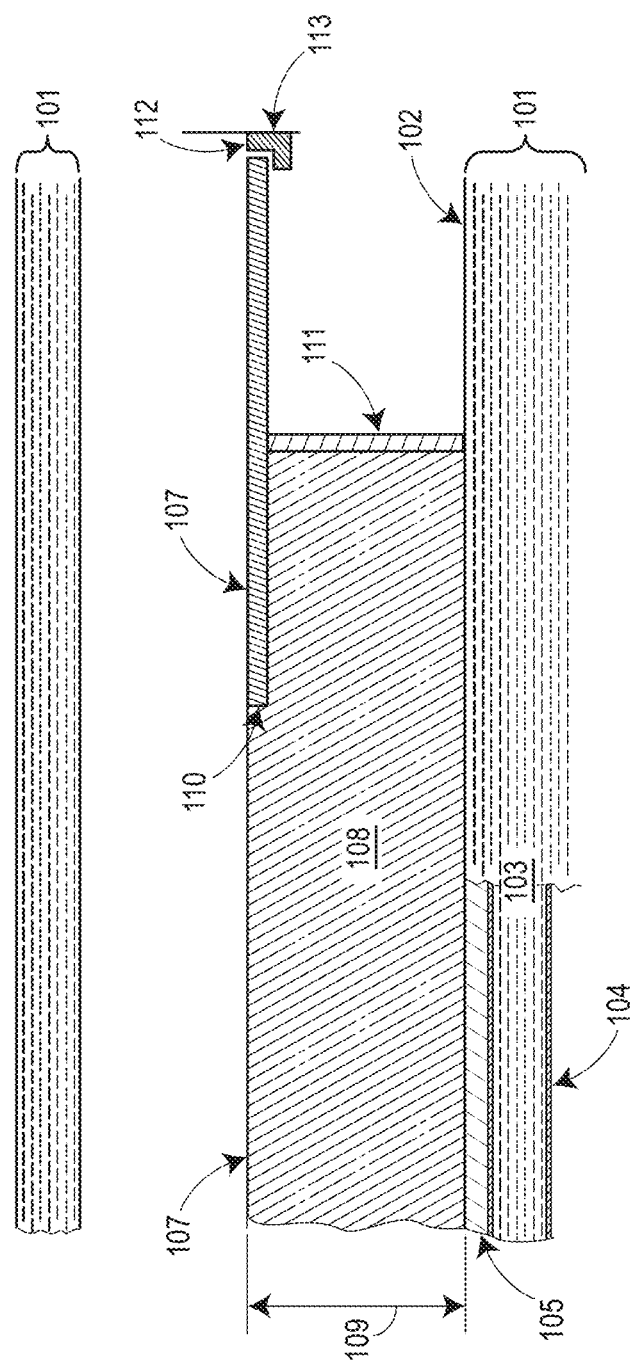
FIG. 3 is another composite drawing of an article showing an arrangement of a plurality of heat sinks and the location and separation of the heat sink surface and the tray surface.

With reference to FIGS. 1-3, the lyophilization chamber includes a heat sink 101 that facilitates the lowering of the temperature within the chamber. The heat sink 101 includes a heat sink surface 102 that is exposed to the internal volume of the lyophilization chamber and is in thermal communication with a refrigerant 103. The refrigerant 103 can be carried in the heat sink 101 within a refrigerant conduit 104. The refrigerant conduit 104 can carry the heat sink surface 102 or can be in fluid communication with the heat sink surface 102 for example through a heat sink medium 105. The heat sink medium 105 is a thermal conductor, not insulator, and preferably has a thermal conductivity of greater than about 0.25, 0.5, and/or 1 W/mK at 25° C.

According to the novel method described herein, the sample containers 106 do not sit on or in direct, substantial thermal conductivity with the heat sink 101 during freezing. In one embodiment, the sample containers 106 sit on or are carried by a tray surface 107 that is thermally insulated from the heat sink 101. In another embodiment, the sample containers 106 are thermally insulated by being suspended above the heat sink 101.

The tray surface 107 is thermally insulated from the heat sink 101 by a thermal insulator 108. The thermal insulator 108 has a thermal conductivity of less than about 0.2, less than 0.1, and/or less than 0.05 W/mK at 25° C. The thermal insulator 108 can be a gas, a partial or complete vacuum, a paper, a foam (e.g., a foam having flexibility at cryogenic temperatures), a polymeric material, or a combination or other mixture of thereof. The polymeric material can be free of or substantially free of open cells or can be a polymeric foam (e.g., a cured foam). As used herein, the thermal insulator 108 refers to the material, object and/or space that provides thermal insulation from the heat sink 101. Air is still considered a thermal insulator in a method or apparatus wherein the pressure of the air is decreased due to evacuation of the lyophilization chamber.

The level of thermal insulation provided by the thermal insulator 108 can be dependent on the thickness of the thermal insulator 108. This thickness can be measured by the distance 109 from the heat sink surface 102 to the tray surface 107, for example. This distance 109, limited by the internal size of the lyophilization chamber, can be in a range of about 0.5 to about 50 mm, for example, or smaller if the thermal isolation is very high. This distance 109 can be optimized for specific lyophilization chamber volumes and preferably is greater than about 0.5, 0.75, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, or 50 mm. While the distance 109 can be larger than about 10 mm, the volume within the lyophilization device is typically better used by optimizing the distances below about 20 mm. Notably, the distance between the heat sink surface 102 and the tray surface 107 is only limited by the distance between the heat sink surface 102 and the upper heat sink 101 minus the height of a vial 106. The preferred distance 109 can be dependent on the specific model and condition of lyophilization chamber, heat sink, refrigerant, and the like, and is readily optimized by the person of ordinary skill in view of the present disclosure to avoid uneven freezing from top and bottom surfaces of the solution in the container.

In an embodiment where the tray surface 107 is thermally insulated from the heat sink 101, the tray surface 107 is carried by a tray 110, preferably a rigid tray. Notably, the tray surface 107 can be a thermal insulator (e.g., foamed polyurethane) or a thermal conductor (e.g., stainless steel). In such an embodiment the thermal insulator 108 may comprise a gas, a partial vacuum, or a full vacuum.

The tray 110 is preferably maintained at a fixed distance between heat sink surface 102 and the tray surface 107 during freezing. The tray 110 can be spaced from the heat sink surface 102 by the thermal insulator 108 formed in an embodiment to include a spacer 111 positioned between the tray 110 and the heat sink surface 102 or can be spaced from the heat sink surface 102 to form the thermal insulator 108 by operationally engaging the tray 110 to a bracket 112 affixed to an internal surface 113 (e.g., wall) of the lyophilization chamber. In a further embodiment, the tray 110 is maintained at a distance from the heat sink surface 102 to form the thermal insulator 108 by a plurality of struts (not shown) that operationally engage the tray 110 and heat sink surface 102. In an embodiment where a spacer 111 supports the tray 110, the distance from the heat sink surface 102 to the tray surface 107 is the thickness of the spacer 111 plus the thickness of the tray 110. In agreement with the distances disclosed above, the spacer 111 can have a thickness in a range of about 0.5 mm to about 10 mm, about 1 mm to about 9 mm, about 2 mm to about 8 mm, and/or about 3 mm to about 7 mm, for example. The tray 110 can be carried by one or more spacers 111 placed between the heat sink surface 102 and the tray 110.

In another embodiment, the tray 110 can be carried by the thermal insulator 108 comprising a rigid thermal insulator. For example the tray 110 can be a thermal conductor (e.g., stainless steel) and supported by (e.g., resting on) a thermal insulator (e.g., foamed polyurethane). In a further embodiment the rigid thermal insulator can be combined with spacers to carry the tray. In agreement with the distances disclosed above, the rigid thermal insulator (with or without the spacer) can have a thickness in a range of about 0.5 mm to about 10 mm, about 1 mm to about 9 mm, about 2 mm to about 8 mm, and/or about 3 mm to about 7 mm, for example.

The lyophilization device can include a plurality of heat sinks 101 that individually have a heat sink surface 102 in thermal communication with a refrigerant 103. In such a lyophilization device, the heat sinks 101 can be disposed vertically in the lyophilization chamber with respect to each other, forming upper and lower heat sinks 101 (see e.g., FIG. 1). By convention, the lower heat sink surface 102 is disposed between the upper and lower heat sinks and the tray surface 107 is disposed between the upper heat sink 101 and the lower heat sink surface 102. In this arrangement, the thermal insulator 108 is disposed between the tray surface 107 and the lower heat sink 101.

Figure 4:
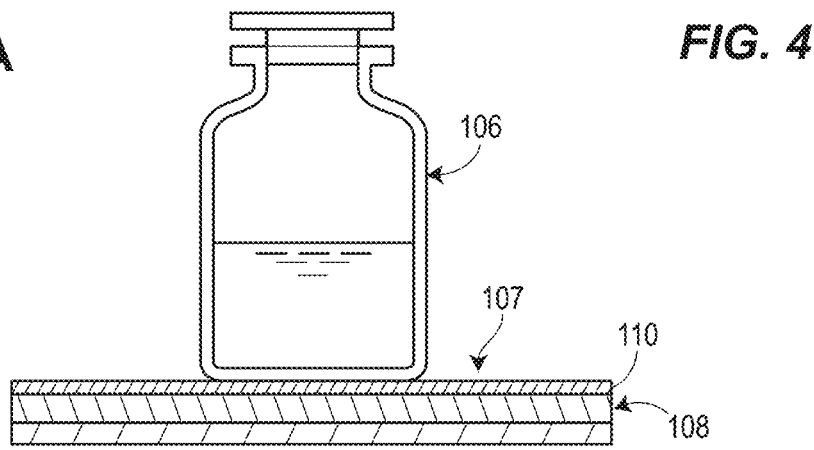
FIG. 4 is illustrations of sample containers, here vials, (4a) positioned on a tray, (4b) positioned directly on a thermal insulator, or (4c) combined with a thermally insulating support.
Figure 4:
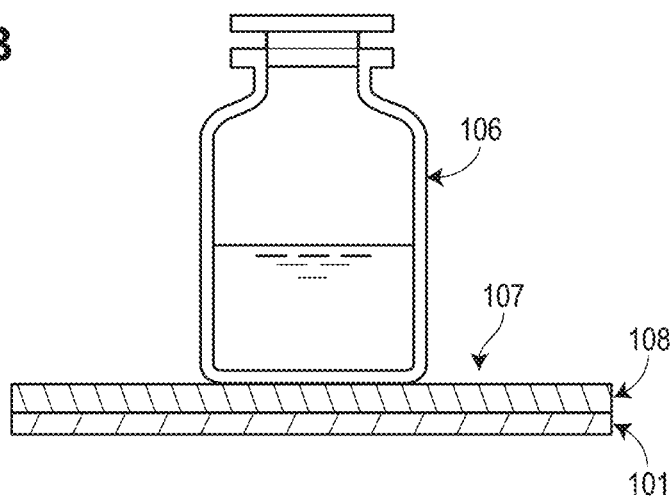
Figure 4:
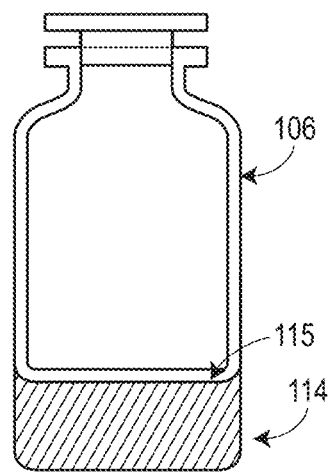

In another embodiment, each individual sample container 106 can sit on or be carried by a thermal insulator 108 (see e.g., FIG. 4b). For example, when the sample container is a vial having a top and a bottom the thermal insulator 108 can comprise a thermally insulating support 114 affixed to the bottom of the vial 115 (see e.g., FIG. 4c). The thermally insulating support 114 can have a thermal conductivity less than about 0.2 W/mK, less than about 0.1 W/mK, and/or less than about 0.05 W/mK at 25° C., for example. In one embodiment, the vial 106 and the insulating support 114 are different materials (e.g., the vial can comprise a glass and the insulating support can comprise a foam or a polymer). The vial can comprise a sealable vial.

Another embodiment of the invention includes a method of freezing a liquid solution for subsequent lyophilization. In one embodiment of the method, the lyophilization chamber as described above is loaded with a liquid solution held in a container that includes a solute (e.g., an active pharmaceutical agent) and a solvent. The liquid solution will have a top surface 116 and a bottom surface, wherein the bottom surface 117 is proximal to the heat sink 101 (see FIG. 5). The container is separated from the heat sink 101 by providing a thermal insulator 108 between the container and the heat sink 101, the thermal insulator having the characteristics described herein. Thus, the container is spaced vertically from the heat sink with an intervening thermal insulator 108, the distance and thermal insulator 108 being selected to provide freezing of the liquid solution from the top and bottom surfaces at approximately the same rate. Having been loaded into the lyophilization chamber, the liquid solution can be frozen by lowering the temperature of the heat sink 101 and thereby the ambient temperature in the lyophilization chamber. The liquid solution advantageously can be frozen from the top and the bottom surfaces at approximately the same rate to form a frozen solution. A further advantage is that the concurrent water to ice conversion at the top and bottom of the solution avoids problematic freeze-concentration and skin formation observed when the bottom of the solution freezes more rapidly than the top.

A further embodiment of the inventions includes once frozen, the liquid solution (now the frozen solution) can be lyophilized to yield a lyophilized cake. In one type of embodiment, the solution is lyophilized without any significant change in the thermal insulator 108 such as by example maintaining the physical arrangement of the container and heat sink elements. In another type of embodiment, the container having the frozen liquid solution is placed in thermally-conductive contact with the heat sink during or following freezing, for example by removing the thermal insulator 108 and placing the tray 107 or containers directly on the shelf. Embodiments of the removal can comprise, removing the spacer 111, moving the brackets 112 or altering the length of the struts (not shown). It is also envisioned that the thermal insulator container not be placed in thermally conductive contact with the heat sink but the insulation characteristics of the thermal insulator 108 be altered such as by significantly lessening the insulation characteristics by reducing the spacing between the tray and heat sink to a minimal distance.

As noted in connection with Example 2 below, when freezing and drying an array of containers, containers placed at the edges of such an array, and those especially at the corners, can experience temperatures which deviate from those of center containers, due to radiant heat from side walls. Thus, in a method of freezing an array of containers, it is contemplated that the thermal insulator 108 or portions thereof between one or more of the container and heat sink can dimensionally vary from the thermal insulator or portions thereof between one or more remaining containers. In an embodiment, the thickness of the thermal insulator 108 can be reduced for edge and/or corner containers, relative to the thickness of the thermal insulator 108 between center containers and heat sink, in order to counter-balance the radiant heating experienced by such edge and corner containers from side walls and thus achieve more consistent temperature profiles across the array.

In this embodiment, the thermal insulator provides for the facile freezing of the liquid solution from the top and the bottom within the lyophilization chamber at approximately the same rate. The freezing of the liquid solution from the top and the bottom can be determined by measuring the temperature of the solution during the freezing process. The temperature can be measured by inserting at least two thermocouples into a vial containing the solution. A first thermocouple 118 can be positioned at the bottom of the solution, at about the center of the vial, for example, and a second thermocouple 119 can be positioned at the top of the solution, just below the surface of the solution, in about the center of the vial, for example. Once a freezing cycle has been optimized for a combination of liquid solution, container configuration, and lyophilization chamber, then in subsequent processing of additional batches temperature monitoring of the containers (e.g. vials) is not necessary.

To freeze the liquid solution from the top and the bottom surfaces at approximately the same rate, the thermal insulator (e.g., type and thickness) can be selected to provide a water-ice conversion index value in a range of about −2° C. to about 2° C., or about −1° C. to about 1° C., and/or about −0.5° C. to about 0.5° C. Preferably, the water-ice conversion index is zero or a positive value. The water-ice conversion index is determined by a method including first plotting the temperatures reported by the thermocouples at the top ($T_t$) and at the bottom ($T_b$) of the solution as a function of time. The water-ice conversion index is the area between the curves, in ° C.·minute, between a first nucleation event and the end of water-ice conversion divided by the water-ice conversion time, in minutes. The water-ice conversion time is the time necessary for the temperature at the top ($T_t$) of the solution to reduce in value below the freezing point plateau for the solution.

The temperature data are collected by loading solution-filled vials into a lyophilization chamber. The lyophilization tray, at t=0 min, is then cooled to about −60° C. The temperature can then be recorded until a time after which the top and the bottom of the solution cool to a temperature below the freezing point plateau.

The areas, positive and negative, are measured from the first nucleation event (observable in the plot of temperatures, e.g., such as in FIG. 6) 122 until both temperature values cool below the freezing point plateau 123. The sum of these areas provides the area between the curves. When calculating the area between the curves, the value is positive when the temperature at the bottom of the vial ($T_b$) is warmer than the temperature at the top of the vial ($T_1$) 120 and the value is negative when the temperature at the top of the vial ($T_t$) is warmer than the temperature at the bottom of the vial ($T_b$) 121. Preferably, the water-ice conversion index is zero or a positive value. This condition will prevent the consequence that the freezing rate at the bottom of the solution is significantly higher than that at the top of the solution. Thus, for example, the water-ice conversion index value in one type of embodiment will be in a range of about 0° C. to about 2° C., or about 0° C. to about 1° C., or about 0° C. to about 0.5° C. For a particular solution and container configuration, the cooling rate, temperature of the tray, and the thermal insulator can be optimized to provide an area between the curves at or near 0° C.·minute. For example, FIG. 7 shows the water-ice conversion indices for 5 wt. % aqueous solutions of sucrose in vials on a stainless steel tray as a function of the distance from the heat sink surface to the stainless steel tray, with the thermal insulator 108 comprising air within a gap between the heat sink surface and the bottom of the stainless steel tray. The tray had a thickness of about 1.2 mm.

Still another embodiment of the invention is a lyophilized cake made by a method disclosed herein. The lyophilized cake can include a substantially dry lyophilized material and a plurality of pores in the lyophilized material having substantially the same pore size. In one embodiment, the lyophilized cake has a pore size that is substantially larger than the pore size of a reference lyophilized cake comprising the same material as the lyophilized cake but made by a standard lyophilization process (e.g., placing a vial 106 comprising a liquid solution onto a heat sink 101 within a lyophilization chamber, excluding a thermal insulator between the vial and the heat sink 101, lowering the temperature of the heat sink 101 and thereby freezing the liquid solution, and then lyophilizing the frozen solution). The cross-sectional area of the cylindrical pores of the lyophilized cake is preferably at least 1.1, 2, and/or 3 times greater than the cross-sectional area of the reference lyophilized cake. In another embodiment the lyophilized cake has a substantially consistent pore size throughout the cake.

The size of pores in the lyophilized cake can be measured by a BET surface area analyzer. The effective pore radius ($r_e$), a measure of the pore size, can be calculated from the measured surface area of the pores (SSA) by assuming cylindrical pores. The effective pore radius $r_e$ can be determined by the equation $r_e = 2\epsilon/\text{SSA} \cdot \rho_s \cdot (1-\epsilon)$ where SSA is the surface area of the pores, $\epsilon$ is the void volume fraction or porosity ($\epsilon = V_{void}/V_{total} = n \cdot r_e^2/V_{total}$), $(1-\epsilon)$ is the solute concentration in the volume fraction units, and $\rho_s$ is the density of the solid.

EXAMPLES

The following examples are provided to illustrate the invention, but are not intended to limit the scope thereof.

Example 1

Figure 5:
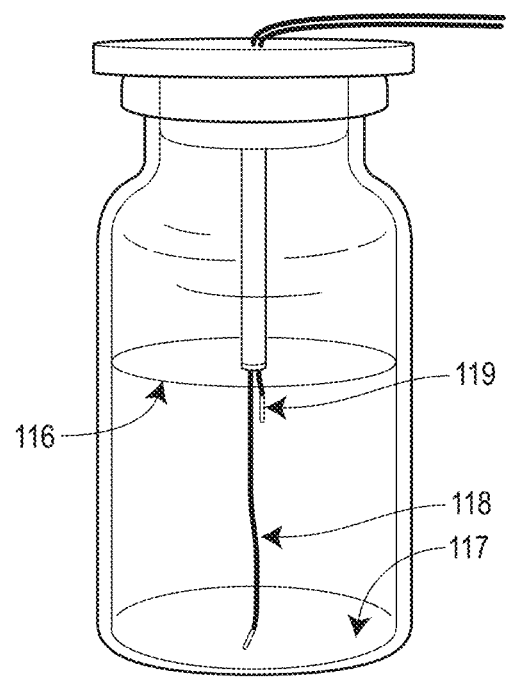
FIG. 5 is a drawing of a sample vial including a liquid solution showing the placement of thermocouples useful for the measurement of the temperatures of the top and the bottom of the solution.

Effect of Gap Freezing on Lowering Product Temperature and on Pore Enlargement The effect of gap freezing on the pore enlargement for a lyophilized 10% aqueous sucrose solution was studied. Multiple 20 mL Schott tubing vials were filled with 7 mL of a 10% aqueous solution of sucrose. These filled vials were placed in a LyoStar II™ (FTS SYSTEMS, INC. Stone Ridge, N.Y.) freeze dryer either directly in contact with a top shelf (heat sink surface) or on a 6 mm gapped tray. See e.g., FIG. 1. Multiple probed vials were produced by inserting two thermocouples into the solutions, one at the bottom-center of the vial and the other one about 2 mm below the liquid surface. See. FIG. 5. The filled vials were then lyophilized by the following procedure:

1) the shelf was cooled to 5° C. and held at this temperature for 60 minutes; next 2) the shelf was cooled to −70° C. and held at this temperature for 200 minutes (the internal temperatures of the thermocouple-containing vials were recorded during freezing);

3) after freezing, the 6 mm gapped tray was removed and these vials were placed directly on the bottom shelf (this provided the vials on the top and bottom shelves with the same shelf heat transfer rate during lyophilization, and thereby a direct comparison of the effect of different freezing methods could be performed); next 4) the lyophilization chamber was evacuated to a set-point of 70 mTorr, and 5) a primary drying cycle, during which time the internal temperatures of the frozen samples were recorded, was started. The primary drying cycle involved (a) holding the samples for 10 minutes at −70° C. and 70 mTorr, then (b) raising the temperature at a rate of 1° C./min to −40° C. while maintaining 70 mTorr, then (c) holding the samples for 60 minutes at −40° C. and 70 mTorr, then (d) raising the temperature at a rate of 0.5° C./min to −25° C. while maintaining 70 mTorr, and then (e) holding the samples for 64 hours at −25° C. and 50 mTorr;

6) a secondary drying followed, and involved raising the temperature at a rate of 0.5° C./min to 30° C. and 100 mTorr, and then holding the samples for 5 hours at 30° C. and 100 mTorr.

The average product temperatures for the frozen samples in vials on the top and bottom (gapped-tray) shelves, during primary drying, are presented in FIG. 8. It can be seen that the temperature profile of the samples on the bottom shelf is much lower than that of those on the top shelf, which implies that the pore size in the dry layer of the bottom shelf samples is much larger than those on the top shelf, due to the effect of "gap-freezing." Theoretically, the temperatures are different from the set point temperatures due to evaporative cooling and/or the insulative effect of larger pore sizes.

The effective pore radius, $r_e$, for the individual lyophilized cakes was determined by a pore diffusion model. See Kuu et al. "Product Mass Transfer Resistance Directly Determined During Freeze-Drying Using Tunable Diode Laser Absorption Spectroscopy (TDLAS) and Pore Diffusion Model."*Pharm. Dev. Technol.* (available online at: http://www.ncbi.nlm.nih.gov/pubmed/20387998 and later published in Vol. 16, no. 4, p. 343-357, 2011) and incorporated herein. The results are presented in FIG. 9, where it can be seen that the pore radius of the cakes on the bottom shelf is much larger than that on the top shelf. The results demonstrate that the 6 mm gapped tray is very effective for pore enlargement.

Example 2

Acceleration of Drying Rate By Removing Gap Following Freezing

An alternative lyophilization procedure was developed to increase the rate of freeze-drying by removing the gap between heat sink shelf and container-loaded shelf following freezing.

Multiple 20 mL Schott tubing vials were filled with 5 mL of a 5% (w/v) aqueous solution of sucrose. Two trays containing these filled vials were placed in a LyoStar II™ (FTS SYSTEMS, INC. Stone Ridge, N.Y.) freeze dryer in the upper and lower portions of the chamber. The trays were separated from contact with the heat sink shelves by a thermal insulator comprising a spacer made of plastic tubing placed on each heat sink shelf, to provide a gap of approximately 6.5 mm between each tray and each heat sink shelf.

For monitoring the product temperature on each shelf, two thermocouples were placed in center vials and six thermocouples were placed on the edge locations of the shelves, as shown in FIGS. 10 and 11, wherein the numbers indicate temperature-probed vials.

The shelf temperature (each) was cooled to −70° C., followed by holding the shelf at −70° C. for 90 minutes. At this low shelf temperature, cooling of vials can be accelerated, since cooling with a gap is primarily driven by radiation. The shelf was then heated to −50° C., followed by holding the shelf at −50° C. for 60 minutes. After the solution was frozen the shelf temperature was raised to a higher temperature of −50° C. because after complete freezing of the solution it is not necessary to maintain it at −70° C. for vacuum pulling. For one of the trays, the thermal insulator 108 was removed prior to vacuum pulling by removing the spacer.

For primary drying: (a) the lyophilization chamber was then evacuated to a set-point of 100 mTorr, (b) the shelf temperature was held at −50° C. (at 100 mTorr) for 30 minutes; (c) the shelf temperature was then ramped to −15° C. (at 100 mTorr) at a rate of 0.5° C./min; and (d) the shelf temperature was then held at −15° C. (at 100 mTorr) until the end of primary drying.

For secondary drying: (e) the shelf temperature was ramped to 30° C. (at 100 mTorr), at a rate of 0.5° C./min; and (f) the shelf temperature was then held at 30° C. (at 100 mTorr) until the end of secondary drying.

Only the temperature profiles of the center vials (TP01, TP02, TP09 and TP10) and the edge vials along the side walls (TP04, TP07, TP12, and TP15) are used for comparison. The product temperature profiles of the corner vials (TP03, TP05, TP06, TP08, TP11, TP13, TP14, and TP16) are not representative for a manufacturing scale freeze dryer due to the strong thermal radiation from the front and back walls to corner vials in this freeze dryer. The front wall of the LyoStar™ II freeze dryer is acrylic without insulation. The back wall of the chamber has insulation, but the large amount of heat produced by the fluid pump penetrates through the insulation and raises the product temperature to some extent.

Comparison for the approximate drying time for vials on the top shelf versus vials on the bottom shelf As shown in FIGS. 12 and 13, the drying time on the top shelf (FIG. 12, thermal insulator remaining during vacuum pulling) is much longer than that on the bottom shelf (FIG. 13, thermal insulator removed before vacuum pulling) due to the much higher heat transfer rate on the bottom shelf without a thermal insulator. It can be seen from FIG. 12 that after approximate 2670 minutes of cycle time, primary drying was still not complete, since the temperature in the center vial, TP02 did not move out of the plateau level during primary drying. On the other hand, FIG. 13 shows that after approximate 1690 minutes of cycle time, primary drying was complete, since the temperatures in the center vials, TP09 and TP10 moved out of the plateau levels of primary drying. Inlet temperatures of the shelf refrigerant fluids are plotted as Tf on each of FIGS. 12 and 13.

Comparison for the product temperatures of center vials, TP01 and TP02 on the top shelf with TP09 and TP10 on the bottom shelf The comparison is shown in FIG. 14, in which the difference between TP02 and TP09 is about 1.7° C.

Comparison for the product temperatures of center vials TP01 and TP02 with the edge vials TP04 and TP07 on the top shelf The comparison is shown in FIG. 15, in which the difference between TP02 and TP07 is about 1.5° C.

Comparison for the product temperatures of center vials TP09 and TP10 with the edge vials TP12 and TP15 on the bottom shelf The comparison is shown in FIG. 16, in which the difference between TP09 and TP12 is only about 0.2° C., which is much smaller than 1.5° C. on the top shelf.

Using the same lyophilization cycle, the vials on the tray without a thermal insulator between the tray and shelf during drying are dried much faster than those with a thermal insulator between the tray and shelf during drying. The tray without a thermal insulator during drying also has the advantage of reducing the temperature difference between the center and edge vials, which could be important for some temperature-sensitive formulations.

A series of non-limiting embodiments is described in the numbered paragraphs below.

1. A method comprising:
loading a container comprising a liquid solution into a lyophilization chamber comprising a heat sink; the liquid solution comprising a solute and a solvent and characterized by a top surface and a bottom surface;
providing a thermal insulator between the container and the heat sink;
lowering the temperature of the heat sink and thereby the ambient temperature in the lyophilization chamber comprising the container and thermal insulator to a temperature sufficient to freeze the liquid solution from the top and the bottom surfaces at approximately the same temperature and form a frozen solution and
altering the thermal insulator during or after the lowering step.

2. The method of the preceding paragraph further comprising reducing the ambient pressure in the chamber to lyophilize the frozen solution.

3. The method of any one of the preceding paragraphs, wherein the container comprises a vial.

4. The method of any one of the preceding paragraphs, wherein the lyophilization chamber comprises a plurality of heat sinks.

5. The method of any one of the preceding paragraphs, comprising loading the container comprising the liquid solution into the lyophilization chamber between two parallel heat sinks.

6. The method of any one of the preceding paragraphs, wherein the heat sink comprises a heat sink surface, the container comprises a bottom, and the thermal insulator comprises a gap between the heat sink surface and the container bottom.

7. The method of any one of the preceding paragraphs, further comprising loading the container comprising the liquid solution onto a tray surface; wherein the thermal insulator is disposed between the tray surface and the heat sink.

8. The method of any one of the preceding paragraphs wherein the altering of the thermal insulator comprises removing the thermal insulator.

9. In a method of freezing a liquid solution for subsequent lyophilization, the liquid comprising top and bottom surfaces and disposed in a container, and the container disposed in a lyophilization chamber comprising a heat sink, the improvement comprising separating the container from direct contact with the heat sink to thereby freeze the solution from the top and bottom surfaces at approximately the same temperature and during or after freezing the solution placing the container in thermal contact with the heat sink during a drying process.

10. A lyophilized cake comprising:
a lyophilized material; and
a plurality of pores in the lyophilized material having substantially the same pore size;
wherein the lyophilized cake is made by the method of paragraph 2.

11. The lyophilized cake of the preceding paragraph, wherein the pore size is substantially larger than the pore size of a reference lyophilized cake; the reference lyophilized cake comprising the same material as the lyophilized cake but made by a method comprising loading a container comprising a liquid solution into a lyophilization chamber comprising a heat sink; the liquid solution comprising the material and a solvent; excluding a thermal insulator between the container and the heat sink; lowering the temperature of the heat sink and thereby the ambient temperature in the lyophilization chamber comprising the container comprising the liquid solution to a temperature sufficient to freeze the liquid solution; freezing the liquid solution; and lyophilizing the frozen solution.

The foregoing description is given for clearness of understanding only, and no unnecessary limitations should be understood therefrom, as modifications within the scope of the invention may be apparent to those having ordinary skill in the art.

What is claimed:

1. A method comprising:
providing a lyophilization chamber comprising a heat sink surface in thermal communication with a refrigerant;
loading a container comprising a liquid solution into the lyophilization chamber, the liquid solution comprising a solute and a solvent and characterized by a top surface and a bottom surface;
forming a thermal insulator between the container and the heat sink surface;
lowering the temperature of the heat sink and thereby the ambient temperature in the lyophilization chamber comprising the container to a temperature sufficient to freeze the liquid solution,
the thermal insulator selected to provide freezing of the liquid solution from the top and the bottom surfaces at approximately the same temperature and thereby form a frozen solution; and
reducing the ambient pressure in the chamber to lyophilize the frozen solution.

2. The method of claim 1, wherein the thermal insulator comprises one of air, a gas, or vacuum space.

3. The method of claim 1, wherein the thermal insulator has a thermal conductivity less than about 0.2 W/mK.

4. The method of claim 2, further comprising providing a tray upon which the container rests between the container and thermal insulator.

5. The method of claim 4, wherein the tray is thermally conductive.

6. The method of claim 4, wherein the tray has a thermal conductivity less than about 0.2 W/mK.

7. The method of claim 1, wherein the heat sink comprises a refrigerant conduit in thermal communication with the heat sink surface.

8. The method of claim 1, wherein the container comprises a vial.

9. The method of claim 6, wherein the thermal insulator comprises a thermally insulating support member affixed to the bottom of the vial, and the thermally insulating support member rests on the heat sink.

10. The method of claim 1, wherein the lyophilization chamber includes at least two parallel heat sinks and further comprising loading the container comprising the liquid solution into the lyophilization chamber between the two parallel heat sinks at distances spaced vertically from each heat sink with an intervening thermal insulator, the distances and thermal insulator selected to provide freezing the liquid solution from the top and the bottom surfaces at approximately the same temperature and thereby form a frozen solution.

11. The method of claim 10, comprising loading an array of such containers comprising liquid solution into the lyophilization chamber, the array thus comprising center containers, edge containers, and optionally corner containers, wherein the dimensions of a portion of the thermal insulator for center containers differ from the dimensions of a portion of the thermal insulator for edge containers.

12. The method of claim 11, wherein the thermal insulator has a thermal conductivity less than about 0.2 W/mK.

13. The method of claim 10, comprising loading an array of such containers comprising liquid solution into the lyophilization chamber, the array thus comprising center containers, edge containers, and optionally corner containers, wherein the thermal conductivity of the portion of the thermal insulator between center containers and heat sink differs from the thermal conductivity of the portion of the thermal insulator between edge containers and heat sink.

14. The method of claim 13, wherein the thermal insulator has a thermal conductivity less than about 0.2 W/mK.

15. The method of claim 1, comprising loading an array of such containers comprising liquid solution into the lyophilization chamber, the array thus comprising center containers, edge containers, and optionally corner containers, wherein the dimensions of a portion of the thermal insulator for center containers differ from the dimensions of a portion of the thermal insulator for edge containers.

16. The method of claim 1, further comprising placing the containers on a tray wherein the thermal insulator comprises a separation distance between the tray and heat sink.

17. The method of claim 1, comprising loading an array of such containers comprising liquid solution into the lyophilization chamber, the array thus comprising center containers, edge containers, and optionally corner containers, wherein the thermal conductivity of the portion of the thermal insulator between center containers and heat sink differs from the thermal conductivity of the portion of the thermal insulator between edge containers and heat sink.

18. The method of claim 1 wherein the forming step includes placing at least one spacer between the container and heat sink.

19. The method of claim 18, further comprising placing the containers on a tray wherein the thermal insulator comprises a separation distance between the tray and heat sink and the at least one spacer is disposed between the tray and heat sink.

20. The method of claim 1, comprising forming the thermal insulator between the bottom of the container and the heat sink surface.

* * * * *